(12) United States Patent
Dahl et al.

(10) Patent No.: US 11,147,975 B2
(45) Date of Patent: Oct. 19, 2021

(54) MEDICAL DEVICE WITH CONVERTIBLE SOLID

(71) Applicant: Cardiac Pacemakers, Inc., St. Paul, MN (US)

(72) Inventors: Scott Dahl, Minneapolis, MN (US); John H. Tangren, Lino Lakes, MN (US); Kevin Ely, Youngsville, NC (US); Douglas J. Brandner, New Brighton, MN (US); William J. Linder, Golden Valley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 740 days.

(21) Appl. No.: 15/365,319

(22) Filed: Nov. 30, 2016

(65) Prior Publication Data

US 2017/0080237 A1    Mar. 23, 2017

Related U.S. Application Data

(63) Continuation of application No. 12/464,655, filed on May 12, 2009, now abandoned.

(60) Provisional application No. 61/053,157, filed on May 14, 2008.

(51) Int. Cl.
*A61N 1/375* (2006.01)
*A61N 1/362* (2006.01)
*A61N 1/39* (2006.01)

(52) U.S. Cl.
CPC .............. *A61N 1/375* (2013.01); *A61N 1/362* (2013.01); *A61N 1/37512* (2017.08); *A61N 1/3968* (2013.01)

(58) Field of Classification Search
CPC .. A61N 1/3756; A61N 1/36125; A61N 1/362; A61N 1/375; A61N 1/3758; A61N 1/36142; A61N 1/3968
USPC .............................................................. 607/2
See application file for complete search history.

(56) References Cited

U.S. PATENT DOCUMENTS

| 4,333,469 A | * | 6/1982 | Jeffcoat | ................... | A61N 1/372 |
|---|---|---|---|---|---|
| | | | | | 607/5 |
| 4,471,783 A | | 9/1984 | Buffet et al. | | |
| 5,411,077 A | | 5/1995 | Tousignant | | |
| 6,222,122 B1 | | 4/2001 | Davidson | | |

(Continued)

OTHER PUBLICATIONS

"U.S. Appl. No. 12/464,655, Advisory Action dated Jul. 30, 2013", 6 pgs.

(Continued)

*Primary Examiner* — Mallika D Fairchild
*Assistant Examiner* — Minh Duc G Pham
(74) *Attorney, Agent, or Firm* — Schwegman Lundberg & Woessner, P.A.

(57) ABSTRACT

Embodiments of the invention are related to medical devices filled with a liquid composition, amongst other things. In an embodiment, the invention includes a hermetically sealed housing defining an interior volume, a component module disposed within the interior volume, the component module comprising a circuit board, the component module displacing a portion of the interior volume. A liquid composition can be disposed within the housing, the liquid composition filling at least 80% of the interior volume not displaced by the component module. Other embodiments are also included herein.

18 Claims, 5 Drawing Sheets

(56) References Cited

U.S. PATENT DOCUMENTS

| | | | |
|---|---|---|---|
| 6,411,854 B1 * | 6/2002 | Tziviskos | A61N 1/375 607/57 |
| 6,820,684 B1 | 11/2004 | Chu et al. | |
| 2005/0119709 A1 | 6/2005 | Gauglitz et al. | |
| 2007/0043306 A1 * | 2/2007 | Olson | A61L 31/14 600/585 |
| 2007/0073218 A1 | 3/2007 | Lau et al. | |
| 2008/0143619 A1 | 6/2008 | Wotherspoon | |
| 2008/0319437 A1 | 12/2008 | Turner et al. | |
| 2009/0287263 A1 | 11/2009 | Dahl et al. | |

OTHER PUBLICATIONS

"U.S. Appl. No. 12/464,655, Appeal Brief filed Oct. 28, 2013", 24 pgs.

"U.S. Appl. No. 12/464,655, Appeal Decision dated Sep. 30, 2016", 10 pgs.

"U.S. Appl. No. 12/464,655, Decision on Pre-Appeal Brief dated Sep. 17, 2013", 4 pgs.

"U.S. Appl. No. 12/464,655, Examiner's Answer dated Feb. 14, 2014", 11 pgs.

"U.S. Appl. No. 12/464,655, Final Office Action dated Apr. 24, 2013", 14 pgs.

"U.S. Appl. No. 12/464,655, Non Final Office Action dated May 14, 2012", 16 pgs.

"U.S. Appl. No. 12/464,655, Non Final Office Action dated Oct. 6, 2011", 14 pgs.

"U.S. Appl. No. 12/464,655, Pre Appeal Brief Request filed Aug. 26, 2013", 7 pgs.

"U.S. Appl. No. 12/464,655, Response filed Jan. 6, 2012 to Non Final Office Action dated Oct. 6, 2011", 10 pgs.

"U.S. Appl. No. 12/464,655, Response filed Jun. 24, 2013 to Final Office Action dated Apr. 24, 2013", 10 pgs.

"U.S. Appl. No. 12/464,655, Response filed Sep. 11, 2012 to Non Final Office Action dated May 14, 2012", 9 pgs.

* cited by examiner

MEDICAL DEVICE WITH CONVERTIBLE SOLID

CLAIM OF PRIORITY

This application is a continuation of U.S. application Ser. No. 12/464,655, filed May 12, 2009, which claims the benefit of U.S. Provisional Application No. 61/053,157, filed May 14, 2008, the content of each of which is herein incorporated by reference.

TECHNICAL FIELD

This disclosure relates generally to medical devices and, more particularly, to medical devices including a liquid filled housing, amongst other things.

BACKGROUND OF THE INVENTION

Some medical devices include a housing that holds and protects electronic components. By way of example, implantable cardiac rhythm management (CRM) devices such as pacemakers and implantable cardioverter defibrillators frequently include a housing that hermetically seals off an interior volume. Components, such as electronic components, used to generate and control electrical stimulation pulses are then disposed within the hermetically sealed interior volume of the housing.

Frequently, there is some amount of the volume of the housing that remains unused after the device components are placed within the housing. This space can be referred as the "residual volume" or the "free interior volume". In some circumstances, this residual volume has simply been filled with ambient air. In other circumstances, the residual volume of housings has been filled with a non-reactive gas such as pure nitrogen. In still other circumstances, the residual volume of housings has been filled with a solid such as an epoxy.

SUMMARY OF THE INVENTION

Embodiments of the invention are related to medical devices filled with a liquid composition, amongst other things. In an embodiment, the invention includes a hermetically sealed housing defining an interior volume, a component module within the housing, and a liquid composition disposed within the residual volume of the housing. Embodiments herein can be used in a variety of applications including, but not limited to, implantable medical devices generally, but more specifically, cardiac rhythm management devices, such as pacemakers, cardiac resynchronization therapy (CRT) devices, remodeling control therapy (RCT) devices, cardioverter/defibrillators, and pacemaker-cardioverter/defibrillators.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
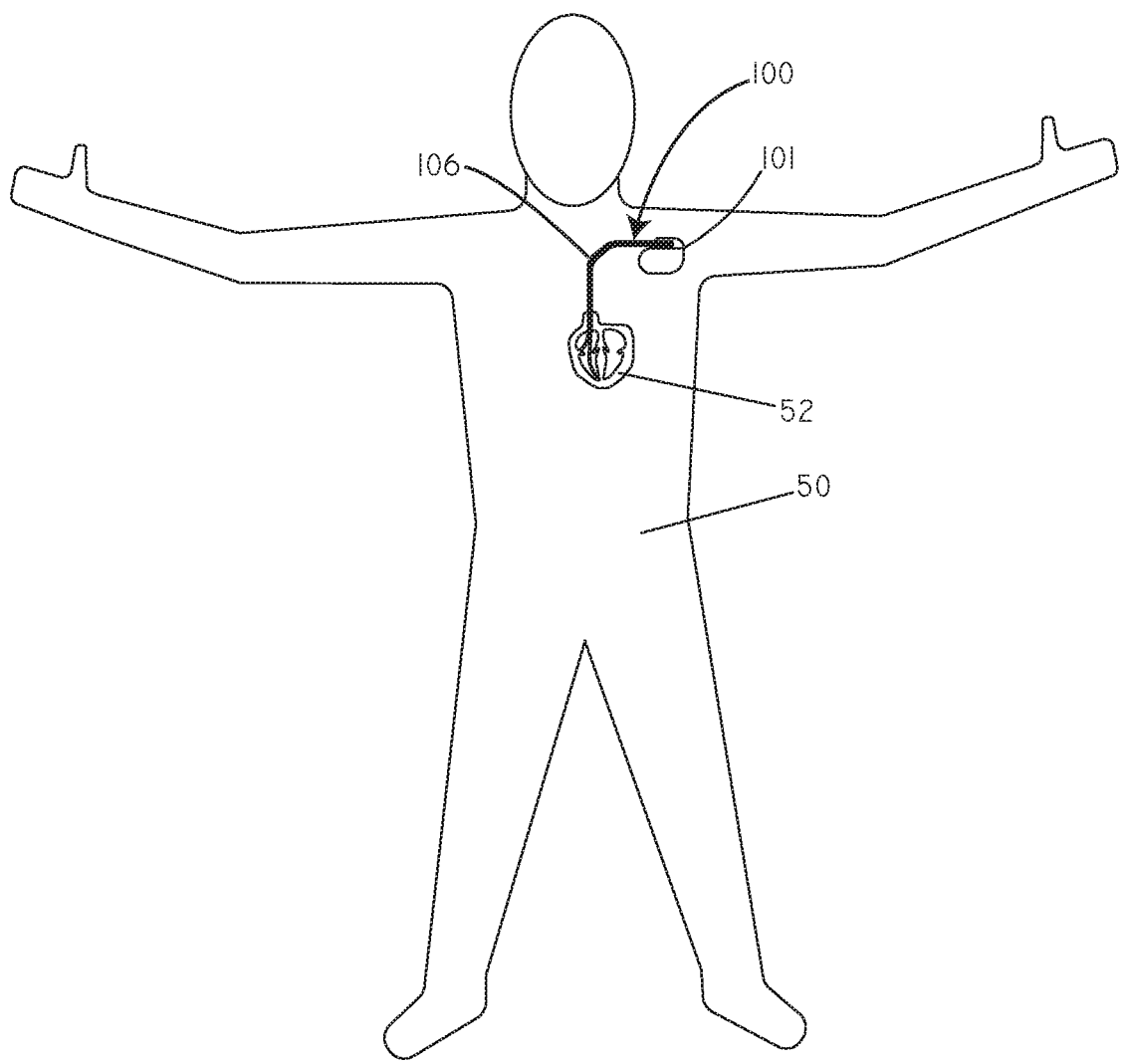
FIG. 1 is a schematic view of a device in accordance with an embodiment disposed within a subject.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Frequently, there is some volumetric amount of a medical device housing that remains unused after the device components are placed within the housing. This unused volume can be referred to as a "residual volume" or "free interior volume". In some instances in the past, this residual volume has simply been filled with ambient air. However, ambient air contains components such as oxygen that can contribute to the degradation of some materials. In other circumstances, the residual volume of housings was filled with a non-reactive gas such as pure nitrogen. In still other circumstances, the residual volume of housings was filled with a solid such as an epoxy. However, a solid can undesirably serve to concentrate stresses inside the housing in certain areas, potentially leading to decreased service life. Furthermore, an epoxy filling can make it very difficult to deconstruct the device for purposes of failure analysis.

Embodiments of the present invention can include medical devices where the residual volume is filled with a liquid composition. In contrast to approaches described above such as filling the residual volume with air, nitrogen, or epoxy, filling the residual volume with a liquid in accordance with embodiments herein can offer various advantages.

In some embodiments the liquid can serve to evenly distribute pressure throughout the interior volume, thereby minimizing stresses on individual components. As such, medical devices in accordance with various embodiments herein can exhibit enhanced durability with respect to forces stemming from pressure changes, shock, vibration, and the like. This is a particularly important benefit in the context of implantable medical devices implanted subpectorally because of the applied forces associated with muscle contraction and breathing.

In some embodiments the liquid filling the residual volume can serve to evenly disperse thermal energy originating inside or outside of the housing. Also, the thermal mass of liquids is generally substantially higher than that of gases on a volumetric basis. As such, the use of a liquid filling in comparison to a gas filling can effectively provide a heat sink within the medical device in order to safely absorb and then dissipate any thermal energy that may exist or form within the housing of the medical device.

In some embodiments the use of a liquid filling in comparison to a gas filling can serve to minimize the presence of water vapor which may otherwise contribute to the deterioration of electronic components.

In some embodiments the use of a liquid filling can serve to enhance longevity of the device because of the lubricious properties of the liquid. When the internal components of a device are bathed in a liquid, the surfaces of the components are less susceptible to any type of frictional wear which may otherwise occur. This is because the liquid effectively makes the surface of such components more lubricious.

In some embodiments the use of a liquid filling in the residual space can facilitate the use of communication techniques that rely on propagation of a pressure wave such as ultrasonic communication techniques. As such in some embodiments, the medical device can include a housing, electronic components disposed within the housing including an ultrasonic emitter and receiver, and a liquid filling the residual space within the housing. In some embodiments the use of a liquid filling can facilitate the transmission of sound, allowing for more efficient sound transmission.

In some embodiments the liquid for filling the residual volume can be selected so as to have a relatively high dielectric strength. As such, the liquid can be highly resistant to dielectric breakdown. Such embodiments can offer increased protection against internal electrical arcing.

In some embodiments the interior volume of the medical device housing can be configured to have a slight positive pressure with respect to the local in vivo environment. This can enhance the rigidity of the medical device housing. In addition, as the liquid can be substantially incompressible, filling the residual volume can serve to preserve any spacing gap in between the wall of the housing and the electronic components contained therein.

Referring now to FIG. 1, a schematic view is shown of an implantable medical system 100 in accordance with an embodiment disposed within the body 50 of a subject. The implantable medical system 100 includes a pulse generator 101 and one or more leads 106. Depending on the configuration, the leads 106 can provide electrical and/or optical communication between the distal ends of the leads 106 and the pulse generator 101. In FIG. 1, the distal ends of the leads 106 are located in the subject's heart 52. However, it will be appreciated that the distal ends of the leads 106 could be disposed in other locations.

In various embodiments, the implantable medical device 100 can include a cardiac rhythm management device, such as a pacemaker, a cardiac resynchronization therapy (CRT) device, a remodeling control therapy (RCT) device, a cardioverter/defibrillator, or a pacemaker-cardioverter/defibrillator. In some embodiments, the implantable medical device 100 can include a neurological stimulation device. It will be appreciated that embodiments of the invention can also be used in conjunction with implantable medical devices that lack pulse generators, but include a housing, such as monitoring devices and drug delivery devices.

Figure 2:
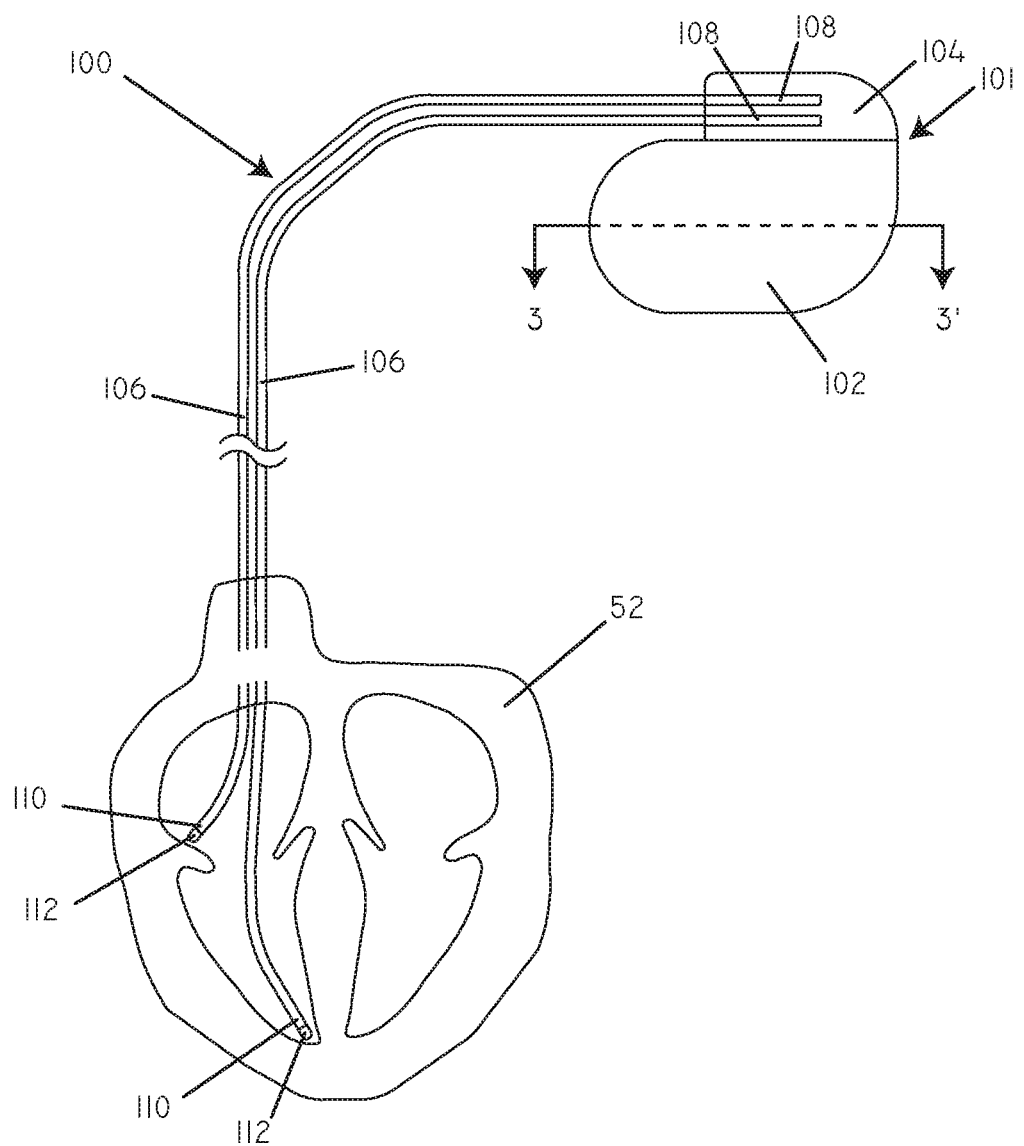
FIG. 2 is a schematic view of an exemplary medical device in accordance with an embodiment.

Referring now to FIG. 2, an enlarged schematic view of the device 100 of FIG. 1 is shown. The pulse generator 101 can include a housing 102 that serves to hold and protect various components of the device, such as a component module or an electronics module. The housing 102 is coupled to a header module 104. The header module 104 can include ports to receive the proximal ends 108 of the leads 106. The header module can be made from various materials such as polymers. The distal ends 110 of the leads 106 can include electrodes 112 that can interface with tissue of the subject's heart 52. However, it will be appreciated that in some embodiments electrodes can be included at locations other than the distal ends of the leads.

Figure 3:
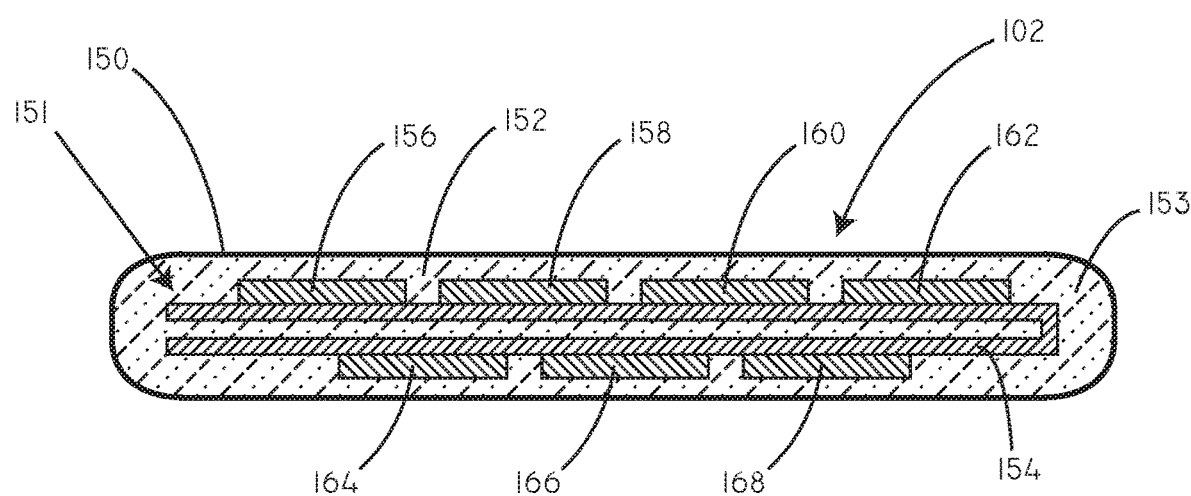
FIG. 3 is a schematic cross-sectional view of an exemplary medical device in accordance with an embodiment.

Referring now to FIG. 3, a cross-sectional schematic view is shown of a housing 102 is shown as taken along line 3-3' of FIG. 2. The housing 102 can include a housing wall 150. The housing wall 150 can be made of various materials including metals, polymers, and ceramics. In some embodiments, the housing wall 150 can be substantially rigid. In other embodiments, the housing wall 150 can be flexible. In a particular embodiment, the housing wall 150 is titanium. The housing wall 150 can define an interior volume 151. Various device components can be disposed within the interior volume 151. For example, a circuit board 154 can be disposed within the interior volume 151. Various electronic components 156, 158, 160, 162, 164, 166, 168 can be mounted on the circuit board 154 within the housing 102. The electronic components can include various items for operation of the device including microprocessors, batteries, capacitors, telemetry modules, amplifiers, transducers, converters, filters, various types of integrated circuit chips (IC chips), and the like. Taken together, the components (other than the liquid composition) within the interior volume can be referred to as a component module. The residual volume 153 is the portion of the interior volume 151 not occupied by the component module.

A liquid composition 152 can be disposed within the residual volume 153. In some embodiments, the liquid composition can substantially fill the residual volume 153. In some embodiments, the liquid composition 152 can fill at least 80% of the residual volume 153. In some embodiments, the liquid composition 152 can fill at least 90% of the residual volume 153. In some embodiments, the liquid composition 152 can fill at least 95% of the residual volume 153. In some embodiments, the liquid composition 152 can fill at least 99% of the residual volume 153.

It will be appreciated that the total volume of the liquid composition used with embodiments herein can vary based on the size of the housing, the percentage of residual volume within the housing with respect to total volume, the degree to which the residual volume is filled, and the like. However, in some embodiments the volume of the liquid composition 152 is between about 0.1 ml to 30 ml. In some embodiments, the volume of the liquid composition 152 is between about 1.0 ml and about 3.0 ml. Aspects of exemplary liquid compositions are described in greater detail below.

The housing 102 can be hermetically sealed. The pressure within the housing 102 can be configured to be at atmospheric pressure (such as equal to 760 mmHg), greater than atmospheric pressure (such as greater than 760 mm Hg), or less than atmospheric pressure (such as less than 760 mm Hg). While not intending to be bound by theory, there can be advantages to configuring the pressure within the housing 102 to be greater than atmospheric pressure. For example, configuring the pressure within the housing 102 can, in effect, enhance the rigidity of the housing 102. As such, where the interior of the housing 102 is at a pressure greater than 760 mm Hg, the housing 102 would be expected to exhibit less flexion in response to normal pressure changes within the body than an otherwise identical housing wherein the interior pressure is at 760 mm Hg. In some embodiments, the pressure within the housing 102 can be greater than 780 mm Hg. In some embodiments, the pressure within the housing 102 can be greater than 800 mm Hg. In some embodiments, the pressure within the housing 102 can be greater than the ambient pressure at the site in the body in which housing 102 is to be implanted.

Figure 4:
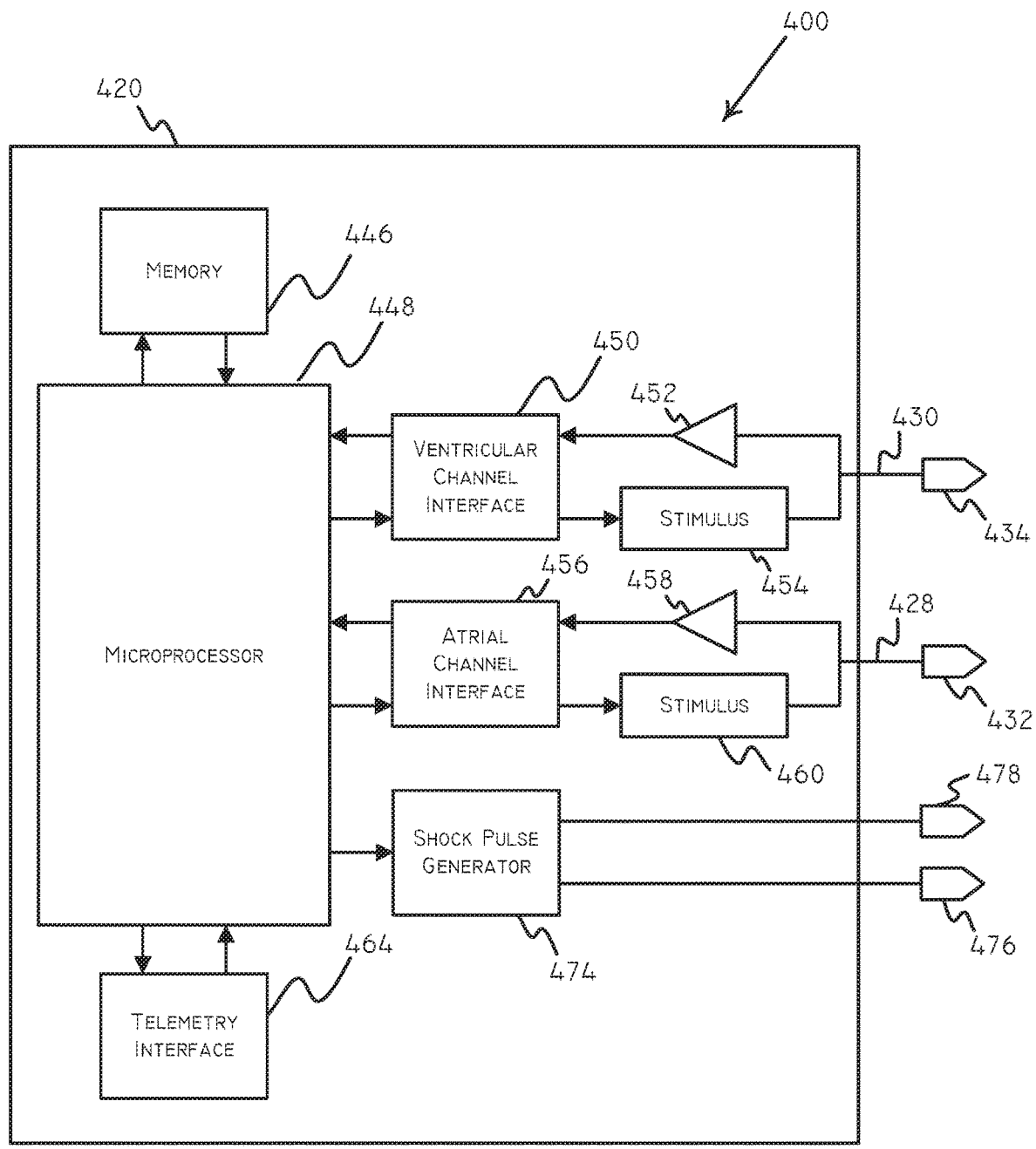
FIG. 4 is a schematic view of components of an exemplary medical device in accordance with an embodiment.

It will be appreciated that various components of a device system can be housed within a housing. Referring now to FIG. 4, some components of an exemplary implantable device system 400 are schematically illustrated. The implantable medical system 400 can include a housing or housing 420 coupled to one or more stimulation leads 430 and 428. Components within the housing 420 can be referred to as a "component module" or an "electronics module". Components within the housing can include a microprocessor 448 (or processor) that communicates with a memory 446 via a bidirectional data bus. The memory 446 typically includes ROM or RAM for program storage and RAM for data storage. The microprocessor 448 can be configured to execute various operations such as processing of signals and execution of methods as described herein. A telemetry interface 464 is also provided for communicating with an external unit, such as a programmer device or a patient management system.

The components can include ventricular sensing and pacing channels including sensing amplifier 452, output circuit 454, and a ventricular channel interface 450 which communicates bidirectionally with a port of microprocessor 448. It will be appreciated that in some embodiments some of the components shown in FIG. 4 may be omitted. Further, in some embodiments, additional elements may be included. By way of example, various embodiments can include a power supply, such as a battery, though not shown in FIG. 4. In addition, various embodiments can include a circuit board (such as that shown in FIG. 3) for purposes of mounting various electronic components.

The ventricular sensing and pacing channel can be in communication with stimulation lead 430 and electrode 434. The device can include atrial sensing and pacing channels including sensing amplifier 458, output circuit 460, and an atrial channel interface 456 which communicates bidirectionally with a port of microprocessor 448. The atrial sensing and pacing channel can be in communication with stimulation lead 428 and electrode 432. For each channel, the same lead and electrode can be used for both sensing and pacing. The channel interfaces 450 and 456 can include analog-to-digital converters for digitizing sensing signal inputs from the sensing amplifiers and registers which can be written to by the microprocessor in order to output pulses, change the pacing pulse amplitude, and adjust the gain and threshold values for the sensing amplifiers. A shock pulse generator 474 can also be interfaced to the microprocessor for delivering defibrillation shocks to the heart via a separate pair of electrodes 476, 478. In some embodiments, electrodes 476 and 478 can be disposed along stimulation lead 430 and stimulation lead 428 respectively.

Figure 5:
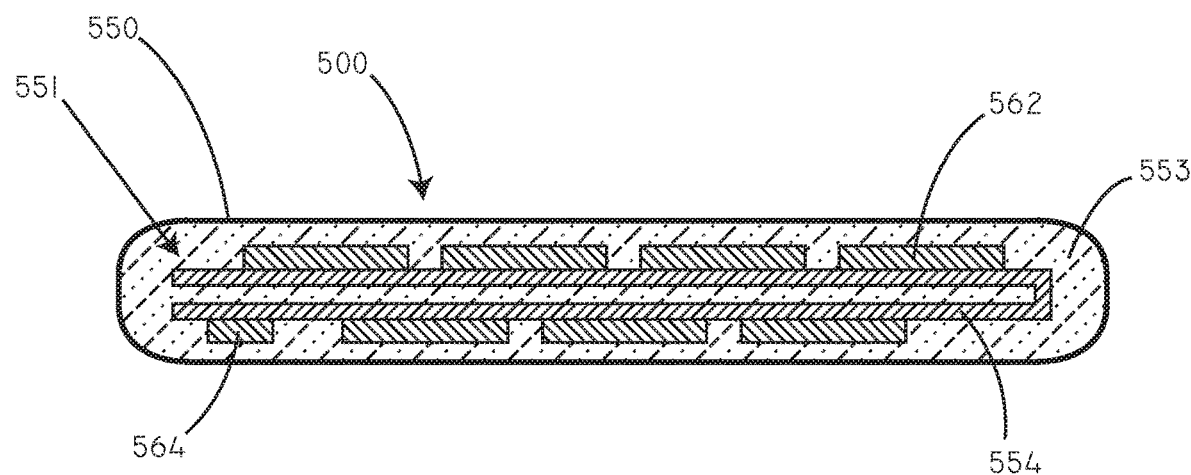
FIG. 5 is a schematic cross-sectional view of an exemplary medical device including a sensor.

It will be appreciated that in some embodiments, devices and systems herein can include sensors. By way of example, as part of the component module of a device, a sensor can be included. The sensor can be disposed within the housing of the device. Referring now to FIG. 5, a schematic cross-sectional view of an exemplary medical device 500 including a sensor 564 is shown. The device 500 can include a housing wall 550. The housing wall 550 can define an interior volume 551. Various device components can be disposed within the interior volume 551. For example, a circuit board 554 can be disposed within the interior volume 551. Various electronic components (such as 562) can be mounted on the circuit board 554 on the inside of the housing wall 550. In this embodiment, the sensor 564 is mounted on the circuit board. However, it will be appreciated that the sensor 564 could also be within the interior volume, but separate from the circuit board 554. The sensor can be, for example, an acoustic sensor, an accelerometer (such as a fluid-filled accelerometer), a temperature sensor, a pressure sensor, or the like.

In some embodiments, the sensor can be part of a switch element, such as a pressure sensitive switch. In such embodiments, the device can be configured to initiate various actions based on switching of the pressure sensitive switch.

Exemplary Liquid Compositions

Embodiments herein can include a housing filled with a liquid composition. The liquid composition can be substantially inert. In some embodiments, the liquid composition can prevent oxidation of electronic components within the housing. In some embodiments, the liquid compositions can be biocompatible.

The liquid composition can have a dielectric strength sufficient to prevent arcing between electronic components within the housing. In some embodiments, the dielectric strength of the liquid composition is greater than about 0.5 kV/mm. In some embodiments, the dielectric strength of the liquid composition is greater than about 1.0 kV/mm. In some embodiments, the dielectric strength of the liquid composition is greater than about 5.0 kV/mm.

In some embodiments, the liquid composition has a kinematic viscosity sufficiently low so that the housing can be filled effectively through an aperture or port. In some embodiments, the liquid composition 213 can have a kinematic viscosity of less than about 20,000 cSt at 25 degrees Celsius. In some embodiments, the liquid composition 213 can have a kinematic viscosity of less than about 10,000 cSt at 25 degrees Celsius. In some embodiments, the liquid composition 213 can have a kinematic viscosity of less than about 1000 cSt at 25 degrees Celsius.

It will be appreciated that the device may be exposed to a variety of different temperatures such as during shipping and storage prior to implantation. The liquid composition can have a thermal expansion coefficient that is relatively small to prevent large pressure changes within the housing. The liquid composition can have a thermal expansion coefficient of less than about 0.1 per degree Celsius. The liquid composition can have a thermal expansion coefficient of less than about 0.01 per degree Celsius. In some embodiments, the liquid composition can have a thermal expansion coefficient of less than about 0.001 per degree Celsius.

Exemplary liquid compositions can be in a liquid state at temperatures between about −50 degrees Celsius and 150 degrees Celsius and at pressures between 380 mm Hg (0.5 ATM) and 2280 mm Hg (3.0 ATM). Exemplary liquid compositions can be in a liquid state at temperatures of about 37 degrees Celsius and at pressures between about 720 mm Hg and 800 mm Hg.

In some embodiments, liquid compositions herein can be selected that remain a liquid long term. For example, liquid compositions can be used that remain a liquid for the duration of the medical device. In some embodiments, the liquid is selected so that it can reversibly change from one physical state of matter to another. For example, in some embodiments the liquid can be selected so that it is in a flowable liquid state during a filling operation of the device, then changes to a solid form, then can be converted back to a liquid through the application of heat, electricity, pressure, or the like.

Exemplary liquid compositions can include halogen substituted organic compounds such as fluorocarbons (including perfluorocarbons) and hydrofluoroethers, silicone oils (polysiloxane liquids), mineral oils, and esters. Specific examples can include, but are not limited to, perfluorodecalin, perfluorooctylbromide, perfluorotripropylamine, perfluorotripentylamine, and 1-bromoperfluorooctane. Exemplary liquid compositions are commercially available and sold under the trade names FLUOROMED®, FLUORINERT™, NOVEC®, NUSIL®, and SILIKON®.

Example Fill Methods

Various methods can be used to fill the residual volume of a hermetically sealed housing. In some embodiments, an aperture or hole is formed in the housing in order to allow the insertion of a liquid composition. The hole location(s) for each device can be selected to avoid potential contact with internal electronic components and to facilitate removal of any air bubbles. In other embodiments, the liquid can be in place before the housing is fully formed. By way of example, the component module can be disposed within a bath of the liquid composition and then the housing can be welded in place around the component module within the bath.

In embodiments where an aperture or apertures are formed in the housing, the liquid composition can be introduced into the interior volume by submersing the housing in the liquid composition. In some embodiments, a syringe or similar instrument can be used to inject the liquid composition into the housing.

In embodiments where an aperture or apertures are formed in the housing, the apertures can be plugged or sealed after the liquid composition is inserted. As an example, the apertures or holes can be sealed by welding a small titanium sphere over them. In another example, a titanium patch can be laser welded over the aperture(s).

The present invention may be better understood with reference to the following examples. These examples are intended to be representative of specific embodiments of the invention, and are not intended as limiting the scope of the invention.

EXAMPLES

Example 1

Device HALT (Highly Accelerated Life Test) Testing Performance

CRM devices with titanium housings (RENEWAL DS, Boston Scientific Corporation, Natick, Mass.) were obtained and used for HALT testing. Holes (1.58 mm) were milled in the titanium housings. A liquid composition (perfluorodecalin, FLUOROMED APF-140HP) was inserted into the housing through the holes. Specifically, the device were immersed in the liquid composition. A syringe was also used to insert the liquid composition. The housings were then sealed by welding a titanium sphere over the hole or by welding a titanium patch over the hole.

The liquid composition-filled devices were then tested in a HALT testing chamber. The conditions were ~80° C. and vibration of 60 $G_{rms}$. The test duration was between 8 and 14 hours. The objective was to assess and compare the durability of the liquid filled devices in comparison with similar gas filled devices in response to vibration forces.

Data for the liquid filled devices was then compared with previous HALT testing of gas filled CRM devices. The gas filled devices were tested with a slightly different procedure than the liquid filled devices. Instead of a constant temperature and vibration level, the gas filled devices were tested using a series of step changes in temperature and vibration levels.

Time to failure data for the devices tested in this study are provided in Table 1, below. The data was analyzed using RELIASOFT® Weibull++® v.6 software program. Since only one of the liquid filled devices experienced a failure, the Weibull distribution was calculated using the assumption that the Beta-value of the liquid filled devices is the same as the Beta-value for the gas filled devices. In addition, a MLE (Maximum Likelihood Estimation) analysis method was selected because of the relatively large number of suspended data points.

TABLE 1

HALT testing conditions and results

| Device | Fill | Testing Conditions | | | Time to Failure (Hours) |
|---|---|---|---|---|---|
| | | Temp ° C. | Vibration G(rms) | Duration (Hours) | |
| RENEWAL DS H175 | Liquid | 80 | 60 | 8 | No Failure |
| RENEWAL DS H175 | Liquid | 80 | 60 | 14 | No Failure |
| RENEWAL DS H195 | Liquid | 80 | 60 | 14 | 10.5 |
| RENEWAL DS H175 | Gas | 80 | 60 | 12 | 3 |
| RENEWAL DS H175 | Gas | 80 | 60 | 12 | No Failure |
| RENEWAL DS H177 | Gas | 80 | 60 | 12 | No Failure |
| RENEWAL DS* | Gas | 80 | 60 | 4 | 1-4 |

*represents data for a plurality of device models

The data show that the time to failure for liquid filled devices is approximately six times greater than the time to failure for the gas filled devices. The improved performance was attributed to a viscous damping effect minimizing damage from shock and vibration.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

The invention claimed is:

1. An implantable medical device comprising:
   a hermetically sealed housing defining a cavity;
   a circuit disposed within the cavity; and
   a material disposed within the housing around the circuit, the material being a solid that is convertible into a liquid, wherein the material is convertible from a solid to a liquid through application of heat.

2. The implantable medical device of claim 1, wherein the material is configured to be in a flowable liquid state during a filling operation in which the material is put into the housing and the material changes to a solid form after the filling operation.

3. The implantable medical device of claim 1, wherein the material is convertible from a solid to a liquid through application of electricity.

4. The implantable medical device of claim 1, wherein the material is convertible from a solid to a liquid through application of pressure.

5. The implantable medical device of claim 1, wherein the material is inert to avoid degradation of the circuit.

6. The implantable medical device of claim 1, wherein the material includes a halogen substituted organic compound.

7. The implantable medical device of claim 1, wherein the material includes a fluorocarbon, hydrofluoroether, silicone oils, mineral oil, or esters.

8. The implantable medical device of claim 1, wherein the material includes mineral oil.

9. An implantable medical device comprising:
a hermetically sealed housing defining a cavity;
a circuit disposed within the cavity; and
a flowed solid material disposed within the housing around the circuit, the material being reversibly changeable from one physical state of matter to another, wherein the material is configured to be in a flowable liquid state during a filling operation, and then changes to a solid form, wherein the flowed solid material is convertible from a solid to a liquid through application of heat.

10. The implantable medical device of claim 9, wherein the flowed solid material is inert.

11. The implantable medical device of claim 9, wherein the flowed solid material is convertible from a solid to a liquid through application of pressure.

12. The implantable medical device of claim 9, wherein the flowed solid material is convertible from a solid to a liquid through application of electricity.

13. An implantable medical device comprising:
a hermetically sealed housing defining a cavity;
a circuit disposed within the cavity; and
a solid material disposed within the housing around the circuit, the material being a solid at 37 degrees Celsius, and the material being convertible into a liquid through application of heat.

14. The implantable medical device of claim 13, wherein the material is convertible from a solid to a liquid through the application of pressure or electricity.

15. The implantable medical device of claim 13, wherein the material is inert.

16. The implantable medical device of claim 13, wherein the material is configured to be in a flowable liquid state during a filling operation of the device, and then changes to a solid form.

17. The implantable medical device of claim 13, wherein the device includes an acoustic sensor and the material facilitates transmission of sound.

18. The implantable medical device of claim 13, wherein the material prevents arcing between electronic components within the housing.

* * * * *